(12) United States Patent
Reynolds et al.

(10) Patent No.: US 6,316,608 B1
(45) Date of Patent: Nov. 13, 2001

(54) COMBINED POLYNUCLEOTIDE SEQUENCE AS DISCRETE ASSAY ENDPOINTS

(75) Inventors: Mark A. Reynolds, Pleasanton; Michael Ruvolo, Orinda; Lyle J. Arnold, Jr., Poway, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/532,656

(22) Filed: Mar. 20, 2000

(51) Int. Cl.⁷ .......................... C07H 21/04; C07H 21/00; C07H 21/02; C12Q 1/68; C02F 1/40
(52) U.S. Cl. .................. 536/22.1; 536/25.32; 536/25.4; 536/25.5; 435/6; 435/395; 204/606
(58) Field of Search ..................... 435/6, 395; 536/22.1, 536/25.32, 25.4, 25.5

(56) References Cited

U.S. PATENT DOCUMENTS

| | | |
|---|---|---|
| 5,837,832 | 11/1998 | Chee et al. . |
| 5,843,655 * | 12/1998 | McGall ..................................... 435/6 |
| 5,981,185 * | 11/1999 | Matson et al. ........................... 435/6 |
| 6,037,186 * | 3/2000 | Stimpson ............................... 436/518 |

OTHER PUBLICATIONS

Gentalen, E. and M. Chee, "A novel method for determining linkage between DNA sequences: hybridization to paired probe arrays", *Nuc. Acids Res.*, 27 (6) : 1485–1491 (1999).

* cited by examiner

*Primary Examiner*—Jeffrey Fredman
*Assistant Examiner*—Arun Chakrabarti
(74) *Attorney, Agent, or Firm*—Richard Aron Osman

(57) ABSTRACT

Methods are provide for determining the relative amounts of individual polynucleotides in a complex mixture. The polynucleotides, after fluorescent labeling, are contacted under hybridization conditions with an array having element disposed at discrete locations on a substrate. The elements comprise two or more distinct polynucleotides that are combined prior to arraying. The level of fluorescence associated with each element provides a measure of its relative amount in the mixture.

15 Claims, 5 Drawing Sheets

FIGURE 2.

Seq. ID. No. 1:

5'GCGCAATGTTTTCTTCATTGAAACAGCTGCAAAATTAGAAAACTAAAATAATAACTTTCAAGAT
AACTAAGCCGGGTTGCCCTTTGACCTAGAAGCATCCCTTATAATAACATTATGTGTATGAAAACC
ATGTCAGCAAGAACGGTTACGGATATGGAGTGAAGCAAAATCTTTAAGGATTTATTTACATTGAA
GAGGAGGAGGAAAAAAGAGCCATAAGGTAAAATTCAAATGCATAAATGAAACTGCCCTTCCTTT
TATACTTCCTAACCTTTGCAGGAGAAAAATATATTAAGGACAAAAGAAAAATAGCCGCTATCATT
TCCAACGCTCCGGGAAAAAGAGTGTCATAGAGACCCCTTATCTATTTATCATTTTAATATGATC
TATTCTGGCATAAGTAGCTTCGGATCGATTAAGCGCTATTACAATTGAAGGAGTAACAAATTTTT
GGGTGAAGTTTACCAATTTATTCAATTGATCAAATTTATGGAAGATCCTCAAGAAAAACATAAAA
TTAAAACCTTTATATCCAGAGTTTCAAATTTGTCAAGTTTTTGTTCCCGTTCACTCTTGTTCTGCAT
ATTTTTCCTATTTTTTTGGCTTGTAACTCAAACATGAACTACATCACAAATATATCACGTTACACG
GGAAATATACTTCCCATTGCATGGAAATTAAGACGGAAATAAGGGAGACATGAAAAAGGGTCTT
GGTGGTGTTGCAGTTGGACAATTAAGCCATTCAATGCGATATAAACTATAAATCCCTTTTAAAAG
GGCCTAGACATCTCAGAGACAAAGAACGGTAGCTATTACAAAGGACAGTAAAAGCAAACAGCTT
TAAATTAGATCAGAACATAAGAATCCTTAGAAAAGCCCTTTACCTCGGTATATGTAGA-3'

| F21S1 | 5'-GCGCAATGTTTTCTTCATTGAAACAGCTGCAAAA TTAGAAAACTAAAATAATAACTTT -3' | Seq. ID. No. 2 |
|---|---|---|
| F21S195 | 5'-AGAGGAGGAGGAAAAAAGAGCCATAAGGTAAAA TTCAAATGCATAAATGAAACTGCCCT-3' | Seq. ID. No. 3 |
| F21S420 | 5'-TAAGCGCTATTACAATTGAAGGAGTAACAAATTT TTGGGTGAAGTTTACCAATTTATTC-3' | Seq. ID. No. 4 |
| F21S784 | 5'-GCCTAGACATCTCAGAGACAAAGAACGGTAGCT ATTACAAAGGACAGTAAAAGCAAACA-3' | Seq. ID. No. 5 |
| F21S843 | 5'-GCTTTAAATTAGATCAGAACATAAGAATCCTTA GAAAAGCCCTTTACCTCGGTATATGT-3' | Seq. ID. No. 6 |

COMBINED POLYNUCLEOTIDE SEQUENCE AS DISCRETE ASSAY ENDPOINTS

FIELD OF INVENTION

The field of invention relates to arrays and microarrays.

BACKGROUND OF THE INVENTION

Microarrays having a plurality of polymeric molecules spatially distributed over and stably associated with the surface of a substantially planer substrate are becoming an increasingly important tool in molecular biology and related fields. Microarrays of both polypeptide and polynucleotides have been developed and find use in a variety of applications, such as gene sequencing, monitoring gene expression, gene mapping, bacterial identification, drug discovery, and combinatorial chemistry. One area in particular in which microarrays find use is in gene expression analysis.

The current methods of manufacturing microarrays employ a single polynucleotide sequence within each assay element on the microarray. For example, U.S. Pat. No. 5,445,934 discloses a method of on-chip synthesis. In this process, the substrate is derivatized with a chemical species containing a photocleavable protecting group. Selected sites are deprotected by irradiation through a mask. The deprotected sites are then reacted with a DNA monomer containing a photoprotective group. The process of masking, deprotecting and reacting is repeated for each monomer attached until an array of site-specific sequences is achieved. Alternatively, the oligonucleotides may be synthesized directly on modified substrates using ink-jet printing methods disclosed in U.S. Pat. No. 6,015,880. In another method, disclosed in U.S. Pat. No. 6,001,309, the sequences are either presynthesized or isolated and then deposited on the substrate.

A typical method of using microarrays involves contacting nucleotide sequences contained in a fluid with the sequences immobilized on the microarrays under hybridization conditions, and then detecting the hybridization complex. The resultant pattern of hybridized nucleic acids provides information regarding the genetic profile of the sample tested. A widely used method for detecting the hybridization complex in microarrays is by fluorescence. In one method, probes derived from a biological sample are prepared in the presence of nucleotides that have been coupled to a fluorescent label (reporter) molecule so as to create labeled probes, and the labeled probes are then incubated with the microarray so that the probe sequences hybridize to the complementary sequences immobilized on the microarray. A scanner is then used to determine the levels and patterns of fluorescence.

The use of fluorescence detection in microarray analysis is disclosed in U.S. Pat. No. 5,888,742 to Lal et al. for the detection of altered expression of human phospholipid binding protein (PLBP) and in U.S. Pat. No. 5,891,674 to Hillman et al. for the monitoring of the expression level of insulin receptor tyrosine kinase substrate (IRS-p53h), and to identify its genetic variants, mutations and polymorphisms for determining gene function, and in developing and monitoring the activity of therapeutic agents.

A disadvantage of these methods is that since each array element contains one polynucleotide sequence, parallel hybridization assays must be carried out in cases where more than one sequence is used to detect a gene transcript. Consequently, the number of elements that must be arrayed in order to detect a plurality of gene transcripts increases. Further increasing the density of the arrays and microarrays is the need to array control elements in order to detect signal variations and cross hybridization reactions. For example, in microarrays, the signal is affected by the sample to sample variation in printing, the quality and hybridization performance of each array element, and the like. As such, there continues to be interest in the development of new methodologies of manufacturing and utilizing microarrays.

SUMMARY OF THE INVENTION

The present invention is directed towards an array of polynucleotides, where each element of the array comprises two or more combined polynucleotide sequences stably associated with the surface of a solid support and arranged in a defined manner.

The invention is also directed towards a method of hybridization where an array of polynucleotides, where each element of the array comprises two or more combined polynucleotide sequences stably associated with the surface of a solid support and arranged in a defined manner is contacted with detectable nucleic acid probes under hybridization conditions to produce a hybridization pattern, and detecting the hybridization pattern.

These and other objectives, advantages, and features of the invention will become apparent to those persons skilled in the art upon reading the details of the invention as more fully described below.

BRIEF DESCRIPTION OF THE DRAWINGS

FIG. 2 provides a schematic representation of the YCF 21 sequence (SEQ ID NO.: 1) and the five complimentary 59mer oligonucleotide of SEQ ID NO.: 2–6.

DETAILED DESCRIPTION

Figure 1:
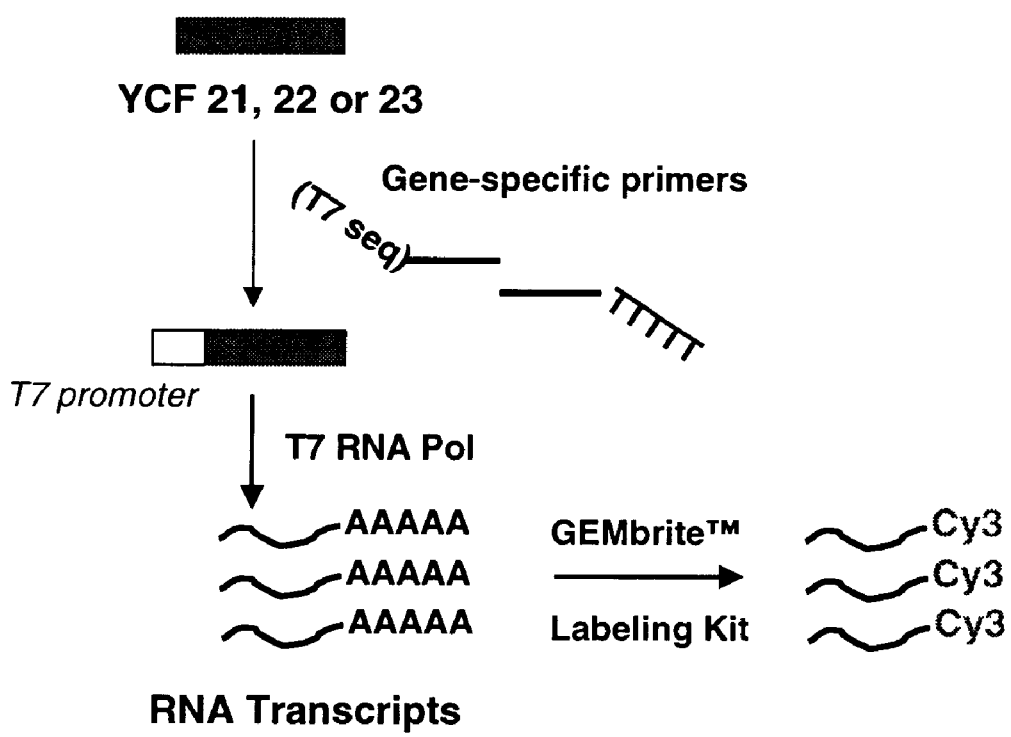
FIG. 1 provides a schematic representation of preparing Cy3-labeled cDNA probes corresponding to yeast control fragments YCF 21, YCF 22 and YCF 23.

Before the present methods and kits are described, it is to be understood that this invention is not limited to particular methods and kits described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Definitions

It must be noted that, as used in the specification and the appended claims, the singular forms "a," "an" and "the" include plural referents unless the context clearly dictates otherwise. Thus, for example, reference to "a probe" means that more than one such probe can be present in the composition. Similarly, reference to "a microarray element" or "the microarray element" includes the possibility of one or more microarray elements, and the like.

The term "probe" or "sample probe" refers to a molecule that is recognized by its complement or a particular microarray element. Examples of probes that can be investigated by this invention include, but are not limited to, DNA, RNA, oligonucleotides, oligosaccharides, polysaccharides, sugars, proteins, peptides, monoclonal antibodies, toxins, viral epitopes, hormones, hormone receptors, enzymes, enzyme substrates, cofactors, and drugs including agonists and antogonists for cell surface receptors.

The term "target," "DNA element" or "microarray element" refers to a molecule that has an affinity for a given sample. Elements may be naturally occurring or synthetic molecules, and may be attached, covalently or noncovalently, to a surface, either directly or via a specific binding substance. Examples of elements which can be employed by this invention include, but are not restricted to, DNA, RNA, oligonucleotides, oligosaccharides, polysaccharides, sugars, proteins, peptides, monoclonal antibodies, toxins, viral epitopes, hormones, hormone receptors, enzymes, enzyme substrates, cofactors, and drugs including agonists and antagonists for cell surface receptors.

The term "complementary" or "complementarity", as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleic acids bind, or it may be complete when total complementarity exists between the single stranded molecules. The degree of complementarity between nucleic acid strands has significant effects on the efficiency and strength of hybridization between nucleic acid strands. Thus, the element and its probe, and the contact area between the element and the probe can be described as complementary.

The term "microarray" refers to an array of targets synthesized or attached or deposited on a substrate, such as plastic, ceramic, paper, nylon or other type of membrane, filter, chip, glass slide, beads, or any other suitable solid support, at high density.

In one embodiment, two or more distinct polynucleotide sequences that are complementary to one or more target polynucleotide sequences, are selected and arrayed as a single element by depositing to the same location on a solid support. The array or the microarray thus manufactured is contacted, under hybridization conditions, with a fluid sample containing labeled nucleic acid probes complementary to the polynucleotide target. The hybridization pattern from the probes is detected to obtain information about the genetic profile of the labeled nucleic acid sample.

In the subject method, two or more distinct polynucleotide sequences that are complementary to one or more target polynucleotide sequences, are selected, combined and arrayed as a single element on a solid support. The distinct polynucleotide sequences that are selected may be from a cloning vector, an oligonucleotide, a polynucleotide, or a full length gene. The distinct polynucleotide sequences may comprise polynucleotides or hybridizing analogues or mimetics thereof, including: nucleic acids in which the phosphodiester linkage has been replaced with a substitute linkage, such as phosphorothioate, methylimino, methylphosphonate, phosphoramidate, guanidine and the like; nucleic acids in which the ribose subunit has been substituted, e.g. hexose phosphodiester; peptide nucleic acids, and the like. The polynucleotide microarray elements may be single or double stranded, and may be PCR fragments amplified from cDNA. The microarray may contain polynucleotides which cover the known 5' or 3' sequence, sequential polynucleotides which cover the full length sequence, or unique oligonucleotides selected from particular areas along the length of the sequence. Polynucleotides used in the microarray may be oligonucleotides that are specific to a gene or genes of interest in which at least a fragment of the sequence is known, or that are specific to one or more unidentified cDNAs which are common to a particular cell type, developmental or disease state. In addition, the microarray elements may comprise combined polynucleotide sequences that may be synthesized by the phophoramidite method or other methods known in the art.

The criteria for selecting the distinct polynucleotide sequences may include the number of nucleotides, the sequence represented, the spacing of the selected polynucleotide sequences when superimposed on the target sequence, overlap between the selected sequences, and the like. According to one embodiment of the invention, the distinct polynucleotide sequences are preferably about 5–10000 nucleotides in length, more preferably about 20–300 nucleotides in length, most preferably about 50–65 nucleotides in length. The distinct polynucleotide sequences are selected such that a particular region of the target polynucleotide, such as a region of high sequence quality, is represented. Depending on the assay to be performed, sequences within the target polynucleotide that are predicted to form hairpins or interstrand structures, such as "primer dimers", may be included or may be excluded. Generally sequences that display significant homology to other non-target sequences in the database are excluded, and spacing algorithms designed to maximize hybridization are used. In general, for a single target polynucleotide, two or more distinct polynucleotide sequences, preferably about two to ten distinct polynucleotide sequences, more preferably about two to five distinct polynucleotide sequences, most preferably, about five different distinct polynucleotide sequences that are complementary to the target sequences may be selected. The selected sequences preferably do not overlap with each other, although some overlap may be desirable for some experiments. In addition, the selected polynucleotide sequences may be complementary to a single target sequence, or to a multiple of target sequences.

The distinct polynucleotide sequences thus selected are combined prior to arraying. In the practice of the invention, the concentration of each distinct polynucleotide sequence may be independently adjusted to the desired level before combining them. The concentration of each polynucleotide with respect to the other selected polynucleotides may vary according to the objectives and requirements of the particular experiment. In the preferred embodiment, each polynucleotide is present in approximately equimolar concentration with respect to the other polynucleotides. Additionally, the total concentration of the combined polynucleotides may be further adjusted such that the hybridization signal is maximized.

The two or more distinct polynucleotide sequences that may be selected and combined as described above, are then arrayed as a single element on a solid support, where the elements are capable of sequence specific hybridization with the nucleic acids of the sample. Thus, each element of the array or the microarray comprises two or more combined polynucleotide sequences. The microarray may be prepared and used according to the methods described in PCT application W095/11995 (Chee et al.), Lockhart, D. J. et al. (1996; Nat. Biotech. 14:1675–1680) and Schena, M. et al. (1996; Proc. Natl;. Acad. Sci. 93:10614–10619), all of which are incorporated herein in their entirety by reference.

The solid support with which the polynucleotide microarray elements are stably associated may be fabricated from a variety of materials, including plastics, ceramics, metals, gels, membranes, glasses, beads, silica, nylon, paper, and the like. The arrays may be produced according to any convenient methodology, such as preforming the polynucleotide microarray elements and then stably associating them with the surface. A number of different array configurations and methods for their production are known to those of skill in the art and disclosed in U.S. Pat. Nos.: 5,445,934, 5,532,128; 5,384,261; and 5,700,637; the disclosure of which are herein incorporated in their entirety by reference. For example, the combined polynucleotides may be stably associated with the substrate through covalent or noncovalent means. In the case where the combined polynucleotides are to be covalently attached to the substrate surface, the substrate includes or is treated to include chemical groups, such as silylated glass, hydroxyl, carboxyl, amine, aldehyde, or sulfhydryl groups. After deposition of the combined polynucleotides, on the substrate surface, they are fixed to each array location by covalent attachment means. This may be done, for example, by drying the combined polynucleotide spots on the array surface, and exposing the surface to a solution of a cross-linking agent, such as glutaraldehyde, borohydride, or any of a number of available bifunctional agents. Alternatively, the combined polynucleotides may be bound to the substrate through covalent means, such as via an alkylamino-linker group or by coating the glass slides with polyethylenimine followed by activation with cyanuric chloride for coupling the oligonucleotides. Alternatively, the combined polynucleotides may be attached to the substrate surface non-covalently, typically by electrostatic interaction between positively charged surface groups and the negatively charged polynucleotides. In one embodiment, the substrate is a glass slide having formed on its surface a coating of a polycationic polymer, preferably a cationic polypeptide, by methods well known in the art. Additionally, the combined polynucleotides may be stably associated with the substrate through a combination of covalent and non-covalent means.

In order to conduct sample analysis using the microarrays, the RNA or DNA from a biological sample is made into hybridization probes. The probe nucleic acids will generally be a DNA that has been reverse transcribed from RNA derived usually from a naturally occurring source, where the RNA could be total RNA, PolyA+mRNA, amplified RNA and the like. The initial mRNA sample may be derived from a physiological source including a single celled organism such as yeast, from a eukaryotic source, or a multicellular organism including plants and animals, particularly mammals and organs, tissues, and cells derived from the mammals such as from any bodily fluids (such as blood, cerebrospinal fluid, urine, saliva, phlegm, gastric juices, etc.), cultured cells, biopsies, or other tissue preparations. Methods of isolating RNA from cells, tissues, organs or whole organisms are known to those of skill in the art and are described in Maniatis et al. (1989); Molecular Cloning: A Laboratory Manual (Cold Spring Harbor Press).

The mRNA is isolated, and cDNA is produced and used as probes for hybridizing to the targets. The probes may be labeled with radioisotopes, chemiluminescent compounds, heavy metal atoms, spectroscopic markers, magnetic markers, linked enzymes, fluorescent labels, and the like. A fluorescent label may be introduced into the probe directly as dye- bearing nucleotides, or bound after amplification using dye-streptavidin complexes to incorporated biotin containing nucleotides. For DNA produced by asymmetric PCR, fluorescent dye is linked directly to the 5' end of the primer. The fluorescent labels are chosen such that they absorb light at wavelengths greater than 250 nm, preferably at wavelengths greater than about 350 nm, and fluoresce at wavelengths about 10 nm higher than the absorption wavelength. The fluorescent label may, for example, be fluorescein (absorption maximum of 488 nm), dichloro-fluorescein (absorption maximum of 525 nm), hexachloro-fluorescein (absorption maximum of 529 nm), BODIPY™ (absorption maximum of 530 nm), ROX (absorption maximum of 550 nm), tetramethylrhodamine (absorption maximum of 550 nm), rodamine X (absorption maximum of 575 nm), Cy2™ (absorption maximum of 505 nm), Cy3™ (absorption maximum of 550 nm), Cy5™ M (absorption maximum of 650 nm), Cy7™ (absorption maximum of 750 nm), IRD40 (absorption maximum of 785 nm), and the like, and further described in Smith et al. (1986); Nature 321: 647–649).

Suitable hybridization conditions are well known to those of skill in the art and reviewed in WO 95/21944 to Maniatis et al. Incubation conditions are adjusted so that hybridization occurs with precise complementary matches or with various degrees of less complementarity. Each element of the array of the invention may hybridize to a single target polynucleotide or to different target polynucleotides. After removal of nonhybridized probes, a scanner, such as a fluorescence scanner, is used for detection or visualization to determine the levels and patterns of fluorescence. A detection system may be used to measure the absence, presence, and amount of hybridization for all of the distinct sequences simultaneously.

The hybridization pattern can be used to determine quantitative information about the genetic profile of the nucleic acids in the sample that was contacted with the array to generate the hybridization pattern, as well as the physiological source from which the labeled sample nucleic acid was derived. The data provides information about the physiological source from which the sample nucleic acid were derived, such as the types of genes expressed in the tissue or cell which is the physiological source, as well as the levels of expression of each gene, particularly in quantitative terms.

The present method can be used in comparing nucleic acid samples from two or more physiological sources to identify and quantify differences between the patterns thereby providing data on the differential expression of a particular gene in the physiological sources being compared. Thus the methods of the invention find use in differential gene expression assays for the analysis of a diseased and normal tissue, analysis of a different tissue or subtissue types, and the like. Thus, this data may be used for large scale correlation studies on the sequences, mutations, variants, or polymorphisms among samples.

In an alternative embodiment, the distinct polynucleotide sequences may be single stranded, double stranded, or hairpins. The distinct polynucleotide sequences may consist of both the sense and the antisense complement to the target sequence. The sense and antisense complements to the target sequence may be selected as described in more detail above, and may be present in any stoichiometry, but are generally present in approximately equimolar concentrations in the reaction fluid. In addition, the sense and antisense sequences can be covalently attached using a variety of methods. In one method, the two strands can be linked as a hairpin. Additionally, the strands can be synthesized as a double hairpin and/or ligated to form a closed dumbell (Annu. Rev. Biophys, Biomol. Struct., 25, 1–28, (1996)). Other methods include covalently coupling the sense and antisense strands using standard chemical approaches. One such method of coupling incorporates linker-arms in the complementary strand, where the linker-arm is modified to react primarily with a functional moiety. Convenient moieties would be the reaction of alkylamines that have been introduced in one strand with active esters, active amides, active imines, aldehydes, bromoacetamides, thiocyanates, and the like as is well known to one skilled in the art. Other convenient coupling moieties include thiols in one strand and disulfides, maleimides, and bromoacetamides in the other strand (see for example, Bioconjugate Chemistry, 1, 165–187 (1990) and references contained therein). Such couples can be positioned at one end, the other end, at both ends, or across an interior portion of the two strands. Two or more double stranded polynucleotides are combined and arrayed onto the solid substrate as described in more detail above. Alternatively, the sense and the antisense sequences can be selected from different portions of the probe sequence such that they are not complementary to each other and may be synthesized in a single sequence such that a portion is complementary to the probe in a sense orientation and a separate portion may be complementary to the prove in an antisense orientation. As a result, this single sequence would bind a probe generated from a mRNA without regard to the orientation of the probe produced from the specific mRNA. Such sense and antisense sequences can then be combined as described above.

One advantage of the present invention is that it reduces the variation in hybridization signals from element to element. In the art methods of manufacturing and using arrays and microarrays of short polynucleotides (e.g. about 20–70 nt), a wide variation in hybridization signals from element to element is observed. The variation in the signal is thought to be caused by variations in binding affinity and variations in accessibility of the labeled target sequences. For example, polynucleotides that are complementary to regions of target sequences that have a high degree of secondary structure (e.g. hairpins) typically display low hybridization signals, whereas those that are complementary to relatively unstructured and accessible regions display high hybridization signals. To date, computer algorithms designed to predict secondary structures have shown relatively low practical utility. Thus, the process of identifying preferred polynucleotides (i.e. those that hybridize efficiently and specifically to target polynucleotides) is essentially empirical, often requiring several rounds of design optimization and experimentation. In the subject method, as shown in Example 2, combining two or more polynucleotides into a discrete assay (e.g. microarray spot or element) enhances the probability of achieving an optimal hybridization signal. Thus, assay performance can be optimized through statistical probability rather than iterative experimentation.

Another advantage of the present invention is that combinations of two or more polynucleotides into a discrete assay have shown increased hybridization signals compared to single polynucleotides (Example 3). One possible explanation for this result is that two or more polynucleotides can hybridize more sequences of labeled probes generated from the target polynucleotide than a single polynucleotide. In addition, the art methods require that parallel hybridization assays must be carried out, that dictate a biochip having a high density of elements. The method of the present invention allow for obtain a large amount of information without resorting to higher density of elements on the biochips.

Also provided are kits for carrying out the invention, where such kits include one or more of the arrays or microarrays having a plurality of elements, fabricated such that each element contain the combined polynucleotide sequences, and instructional material for carrying out the subject methodology. The kit may also include one or more additional components necessary for carrying out the gene expression of the subject invention, where such additional components include enzymes, e.g. polymerases, reverse transcriptases, endonucleoses, dNTPs, buffers, and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperatures, etc.) but some experimental errors and deviations should be accounted for. Unless indicated otherwise, parts are parts by weight, molecular weight is weight average. molecular weight, temperature is in degrees Centigrade, and pressure is at or near atmospheric.

The cDNA microarrays, made according to U.S. Pat. No. 5,807,522 to Brown et al., were provided by Incyte Pharmaceuticals, Inc. The oligonucleotides were synthesized and purified by Operon Technologies, and used without further purification.

Example 1

The probes for the detection of yeast control fragment sequences YCF 21, YCF 22, and YCF 23 were prepared as shown in FIG. 1. The PCR transcripts were made using gene-specific primers, wherein one contained a T7 promoter sequence and the other contained a poly-dT sequence. The resulting PCR amplicons were used to generate RNA transcripts using T7 RNA Polymerase. RNA transcripts were quantitated by absorbance (260 nm) and fluorescence (RiboGreen). Next, RNA transcripts corresponding to each yeast control fragment (1 ng each) were combined and labeled with a GEMbrite™ kit to generate Cy5-labeled cDNA probes.

Example 2

This example serves to demonstrate a method of the present invention using combined polynucleotides as elements, and also demonstrated increased concentration of fluorophore at each array site using the combined polynucleotides.

For the yeast control fragment YCF 21 having the sequence of SEQ ID No.:1 (shown FIG. 2), five complimentary 59mer oligonucleotide of SEQ ID NO.:2–6 were chosen. For the yeast control fragment YCF 22 having the sequence of SEQ ID No.:7 (shown below),
5' AGTGATAATCCTTACGGAACAATGAGCACA
CAATATATTGATGAGACAGCATTTGTTCAGGCT
GAGCAAGGTAAAACCAATCTAATGTTCTCTGAC GAAAAGCAACAGGCACGTTTTGAGCTCGGTGTT
TCCATGGTTATTTATAAGTGGGATGCGTTGGATGT
TGCCGTAGAAAACAGTTGGGGTGGTCCAGAC
TCAGCTGAGAAGAGAGACTGGATTACAGGGAT
TGTAGTAGACCTTTTCAAAAATGAAAAAGTTGT
TGACGCCGCTTTAATCGAAGAAACGTTACTTTAT
GCAATGATAGATGAATTTGAAACTAATGTTGAAG
ACGACTCGGCTTTACCGATTGCCGTGGAGGTCAT
CAACATATATAACGACTGTTTCAATTTAAATTA
TAATAAGGTAGAAAAATTGTATTTGGAATGGCAA
GAAAAGCAGAGAACTAAAAAATCAAAAAGA
GTTGTGCATATTGAGGGTGATGATGATGAAGACG
ATGAAGATGTAGAGGACTATGATGACGAAGATGA
AGATGAAGAGATGGACGAGGTTGTACCTGACTTA
GTATCGTCTAAACCTGAACCAATTGTTGACGAAG
ACGGTTTTGAATTGGTTCAACCAAAAGGAAGAA
GAAAGCACTAGTATCTTCAAAATCTGTAT
ATTATAATTGATAGTGCGCTGCTTTTTTGCACTT
CCAGTAAGAAATAGCAACAAAATTAGATAAATCT
CGGTGGAGTTATCCAAAATATGTAATATATATCAA
GAAAGTTACGTATTAAACATTGGACTTCTAGA
GGAGATCTTCAATATAGATTTAAAAGGTGGGCAA
TGCATCGCTACGTGAAGATTTTACTTFTCTTCAAC
ATGTGTATTTTTTATGTTTCATATTTFTATATTTTGT
GTTTGCTAAGGTCTAATCGTTCAGC-3' five complimentary 59mer oligonucleotide of SEQ ID NO.:8–12 were chosen.

TGTTATTFAGAACAGAGTATCAGTATATCGTATGT
CACAGAACAACACAATCAGCTCAATGAATCCT
GAAAGAGCTTACAACAATGTAACGCTGAA
AAATTTAACAGCATTTCAGTTATTATCTCAAAGAG
AAAACATATGCGAGTTATTGAACTTGGTAG
AAAGTACGGAAAGACACAATAGTATTATCAA
TCCTGAAAGGCAAAGGATGAGTTTGGAAGAA
ATGAAAAAAATGCTCGATGCTTTGAAAAATGAA
AGGAAAAAGTAGGAAAACGCAACATTCACAAT
TGTAAGCTACAAAATATTGAATGTGAATCCTG
CTTCATTACAAATGAAGAATTTCAAAGCGTATC
TAGTTCACCAAAAGTCACAATATCTTATTAT
TATTTGGAAGCTTTTATATGCATCTAATGGTCAT
AAATCCCATCTCACTTTATAAAACAAGTTACCG
CGAATGTATCCAGTGATACAGAATAGAGTGTAAC
AAATGAGAATAAAAATACCATATTATCGTTTA
ATTTTGGTAGGGTACGCTAAAATAAAGTGGTGTT
TGCGTCTCCATATAACTAAAAAGAATTGAAATGG
CCTACTATCGATTAGACTATTCAGGCATGGAA
GCAGTAAGAACATTTCTTGATTTTGGAAAAAT
GAGATTAGATTATTAATTATTATTGAGTTTGTGTA
TATAATTTATTTTGCATATTTCATAAAGAAATTAA
AATTAGATTATTAAATATTAAGTTTCATTAGTG
ACATTAAAAGAAGAAAACTGATGTTTGAAATGT
GTTAAGCAAAGAATGATTAAGACAATCTCAAGC

| F22S1 | 5'-ACGGAACAATGAGCACACAATATATTGATGAGACAGCATTTGTTCAGGCTGAGCAAGGT-3' | Seq.ID.No.8 |
| F22S198 | 5'-GACTGGATTACAGGGATTGTAGTAGACCTTTTCAAAAATGAAAAAGTTGTTGACGCCGC-3' | Seq.ID.No.9 |
| F22S425 | 5'-GAGAACTAAAAAATCAAAAAGAGTTGTGCATATTGAGGGTGATGATGATGAAGACGATG-3' | Seq.ID.No.10 |
| F22S794 | 5'-TAGATTTAAAAGGTGGGCAATGCATCGCTACGTGAAGATTTTTACTTTTCTTCAACATG-3 | Seq.ID.No.11 |
| F22S853 | 5'-TGTATTTTTTATGTTTCATATTTTTATATTTTGTGTTTGCTAAGGTCTAATCGTTCAGC-3' | Seq.ID.No.12 |

For the yeast control fragment YCF 23 having the sequence of SEQ ID No.: 13 (shown below), 5'ATCCGCCACATAAGATGCACAAAATGAGCCTA
TAACATTGAATTTTATGATAGAACGAAAGGATTG
TGCTCTAAGCAGTATCTTCGACAGCTTGCTCTG
CTTCAGGTTCGGGTTCGTG-3' five complementary 59mer oligonucleotide of SEQ ID NO.:14–18 were chosen.

| F23S1 | 5'-ATCCGCCACATAAGATGCACAAAATGAGCCTATAACATTGAATTTTATGATAGAACGAA-3' | Seq.ID.No.14 |
| F23S200 | 5'-AACATATGCGAGTTATTGAACTTGGTAGAAAGTACGGAAAGACACAATAGTATTATCAA-3' | Seq.ID.No.15 |
| F23S431 | 5'-AAGTCACAATATCTTATTATTATTTGGAAGCTTTTATATGCATCTAATGGTCATAAATC-3' | Seq.ID.No.16 |
| F23S805 | 5'-AAGTTTCATTAGTGACATTAAAAGAAGAAAACTGATGTTTTGAAATGTGTTAAGCAAAG-3' | Seq.ID.No.17 |
| F23S846 | 5' AATGATTAAGACAATCTCAAGCTGCTCTAAGCAGTATCTTCGACAGCTTGCTCTGCTTC-3' | Seq.ID.No.18 |

Figure 3:
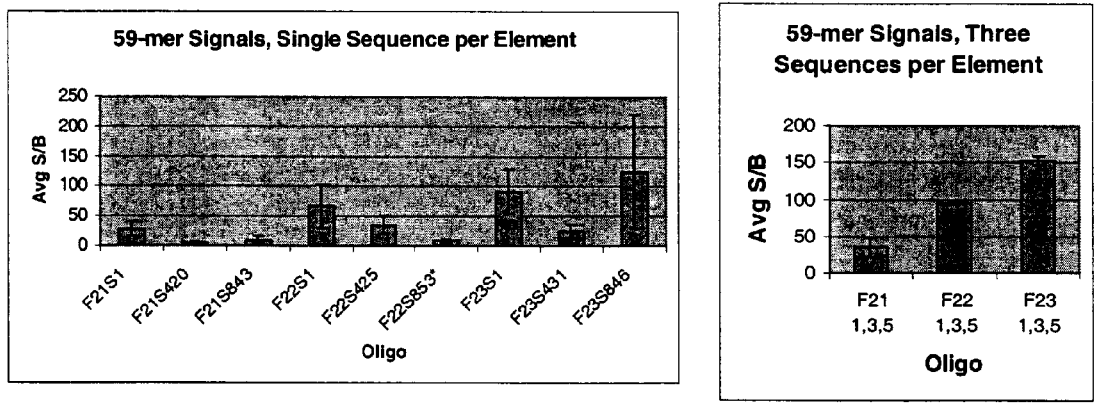
FIG. 3 provides a schematic representation of the hybridization signal from elements comprising single polynucleotides versus combined polynucleotides corresponding to yeast control fragments YCF 21, YCF 22 and YCF 23.

The polynucleotides corresponding to SEQ ID NO.:2–6, SEQ ID NO.:8–12, and SEQ ID NO.:14–18 were individually diluted in 3×SSC buffer to a final concentration of 100 micromolar, and placed in separate wells in a 96-well plate. The polynucleotides corresponding to SEQ ID NO.:2–6 were combined in equal volume in a single well in a 96-well plate. Similarly, the polynucleotides corresponding to SEQ ID NO.:8–12, and SEQ ID NO.:14–18 were combined in equal volume in different 96-well plates. Samples from each well were then arrayed onto P-glass (16 times per slide). The arrayed slides were post processed and then hybridized to Cy5-labeled cDNA probes, generated according to the scheme shown in FIG. 1. Data analysis involved laser scanning and signal processing using GEMTools™ software. The resulting hybridization signals for averaged elements containing single and combined polynucleotides are shown in FIG. 3. This data demonstrates that combined polynucleotides give higher signal response.

Example 3

This example serves to demonstrate a method of the present invention using combined polynucleotides as elements, and also demonstrated increased sensitivity obtained by using the present method.

As in Example 2, the polynucleotides were subject to two fold dilutions from 50 $\mu$M to 6.25 $\mu$M. The five polynucleotides for each fragment were individually arrayed. In addition, the five polynucleotides for each fragment were combined in equal concentration and then arrayed. The arrayed slides were hybridized to Cy3-labeled cDNA probes, and the hybridization pattern detected.

The data was analyzed by averaging the signal from the four replicate elements across the two GEMs with the same probe. Since two transcripts in each probe had the same mass, the targets that correspond to the same probe mass were averaged. For example, if transcripts for F21 and F22 had the same mass in the probe, the signal from the targets was averaged. The dynamic range for the binned elements was determined by plotting the average S/B for the different transcript masses.

Figure 4:
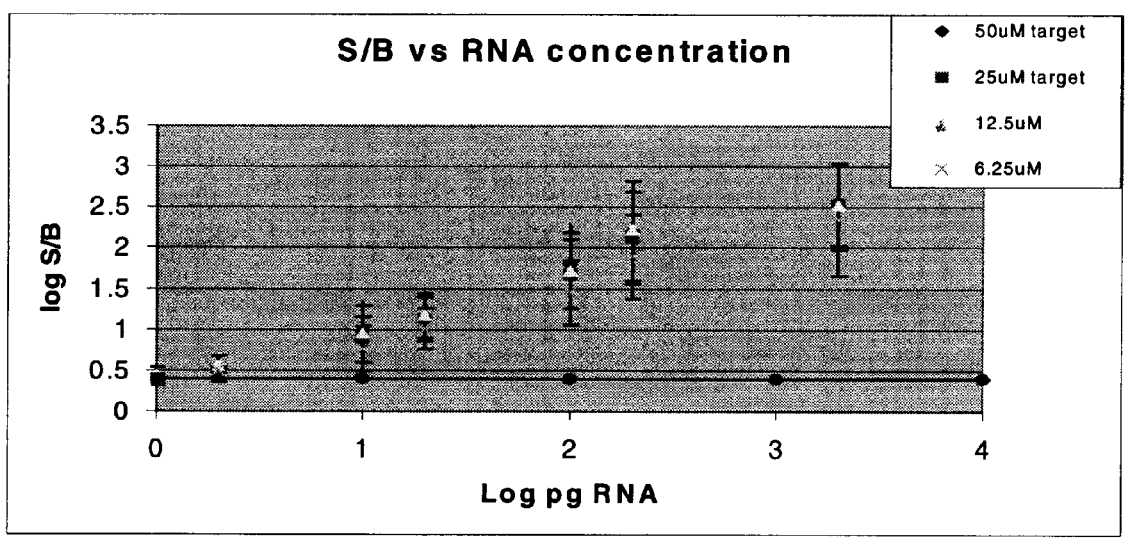
FIG. 4 illustrates the dynamic range of the combined polynucleotide arrays as determined by plotting the average signal to noise ratio for the different transcript masses.

The data (FIG. 4) showed that from 50 to 12.5 $\mu$M elements, the response was the same and at 6.25 $\mu$M the S/B was slightly lower but the dynamic range was still comparable. The points on the graph represent from left to right: 1:200K, 1:100K, 1:20K, 1:10K, 1:2K, 1:1K, 1:100 sensitivity based on transcript mass over total mass of RNA (i.e. 1:100K is 2 pg transcript in 200 ng RNA). The line at the bottom represents 2.5×S/B which is the current cutoff for passing elements in GEMtools. The signal response was fairly linear between 1:100K and 1:1K.

Figure 5:
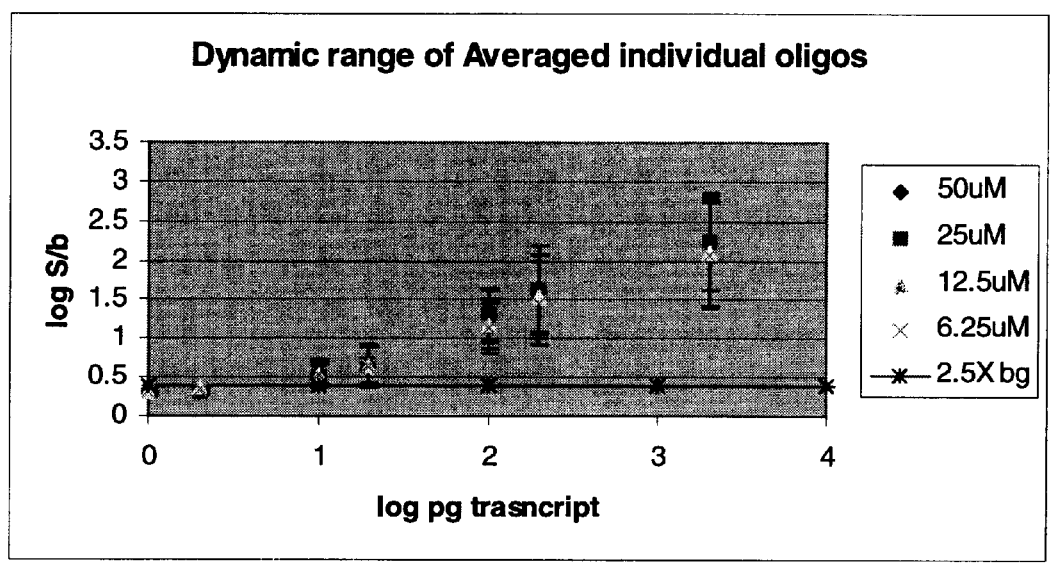
FIG. 5 illustrates the increased performance of the arrays of the present invention as measured by the greater sensitivity at lower transcript levels.

To compare the performance of the elements comprising combined polynucleotides with the elements comprising individual polynucleotides, the same dynamic range curve was plotted using the average of the individual polynucleotides at each transcript concentration (FIG. 5). The data showed that combined polynucleotides provided greater sensitivity at lower transcript levels. Therefore, the dynamic range of the combined polynucleotides was similar to the PCR arrays with linear sensitivity approaching 1:100K abundance of transcript. When the polynucleotides were not combined but averaged across separate elements, the dynamic range is shifted to higher transcript abundance.

What is claimed is:

1. A microarray of non-contiguous polynucleotides, the array comprising:
   a solid support having a surface; and
   a plurality of elements arranged in a defined manner and stably associated with the surface, wherein each element comprises two or more combined, distinct polynucleotides having distinct sequences.

2. The array of claim 1, wherein the solid support is selected from the group consisting of glass, silica, plastic, ceramic, beads, and nylon, and combinations thereof.

3. The array of claim 1, wherein each element comprises about two to about ten combined, distinct polynucleotides having distinct sequences.

4. The array of claim 1, wherein each element comprises about two to about five combined, distinct polynucleotides having distinct sequences.

5. The array of claim 1, wherein the polynucleotide sequences are complementary to a single target polynucleotide.

6. The array of claim 1, wherein the polynucleotides independently comprise from about 5 to about 10000 nucleotides.

7. The array of claim 6, wherein the polynucleotides independently comprise from about 20 to about 300 nucleotides.

8. The array of claim 7, wherein the polynucleotides independently comprise from about 50 to about 65 nucleotides.

9. The array of claim 1, wherein the polynucleotides are double stranded.

10. The array of claim 1, wherein the elements are associated with the surface by non-covalent means.

11. The array of claim 1, wherein the elements are associated with the surface by covalent means.

12. The array of claim 11, wherein the covalent means comprises a linker.

13. The array of claim 1, wherein the elements are associated with the surface by non-covalent and covalent means.

14. A hybridization assay comprising the steps of:

contacting the array of claim 1, 3, 5, 6, or 10 with detectable nucleic acid probes under hybridization conditions to produce a hybridization pattern; and detecting the hybridization pattern.

15. A kit for use in measuring hybridization, comprising:

an array according to claim 1, 3, 5, 6 or 10; and instructional material for measuring hybridization with the array.

* * * * *

SEQUENCE LISTING

<160> NUMBER OF SEQ ID NOS: 18

<210> SEQ ID NO 1
<211> LENGTH: 903
<212> TYPE: DNA
<213> ORGANISM: Candida albicans
<220> FEATURE:
<221> NAME/KEY: misc_feature
<223> OTHER INFORMATION: Incyte ID No: YCF21

<400> SEQUENCE: 1
gcgcaatgtt ttcttcattg aaacagctgc aaaattagaa aactaaaata ataactttca      60
agataactaa gccgggttgc cctttgacct agaagcatcc cttataataa cattatgtgt     120
atgaaaacca tgtcagcaag aacggttacg gatatggagt gaagcaaaat ctttaaggat     180
ttatttacat tgaagaggag gaggaaaaaa gagccataag gtaaaattca aatgcataaa     240
tgaaactgcc cttccttta tacttcctaa cctttgcagg agaaaaatat attaaggaca     300
aaagaaaaat agccgctatc atttccaacg ctccgggaaa aagagtgtca tagagacccc     360
ttatctattt tatcatttt aatatgatct attctggcat aagtagcttc ggatcgatta     420
agcgctatta caattgaagg agtaacaaat ttttgggtga agtttaccaa tttattcaat     480
tgatcaaatt tatggaagat cctcaagaaa aacataaaat taaaaccttt atatccagag     540
tttcaaattt gtcaagtttt tgttcccgtt cactcttgtt ctgcatattt ttcctattt     600

```
tttggcttgt aactcaaaca tgaactacat cacaaatata tcacgttaca cgggaaatat      660
acttcccatt gcatggaaat taagacggaa ataagggaga catgaaaaag ggtcttggtg      720
gtgttgcagt tggacaatta agccattcaa tgcgatataa actataaatc ccttttaaaa      780
gggcctagac atctcagaga caaagaacgg tagctattac aaaggacagt aaaagcaaac      840
agctttaaat tagatcagaa cataagaatc cttagaaaag ccctttacct cggtatatgt      900
aga                                                                   903

<210> SEQ ID NO 2
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F21S1

<400> SEQUENCE: 2
gcgcaatgtt ttcttcattg aaaacagctg caaaattaga aaactaaaat aataacttt       59

<210> SEQ ID NO 3
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F21S195

<400> SEQUENCE: 3
agaggaggag gaaaaaagag ccataaggta aaattcaaat gcataaatga aactgccct       59

<210> SEQ ID NO 4
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F21S420

<400> SEQUENCE: 4
taagcgctat tacaattgaa ggagtaacaa attttgggt gaagtttacc aatttattc        59

<210> SEQ ID NO 5
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F21S784

<400> SEQUENCE: 5
gcctagacat ctcagagaca agaacggta gctattacaa aggacagtaa aagcaaaca        59

<210> SEQ ID NO 6
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F21S843

<400> SEQUENCE: 6
gctttaaatt agatcagaac ataagaatcc ttagaaaagc cctttacctc ggtatatgt       59

<210> SEQ ID NO 7
```

```
<211> LENGTH: 924
<212> TYPE: DNA
<213> ORGANISM: Candida albicans
<220> FEATURE:
<221> NAME/KEY: misc_feature
<223> OTHER INFORMATION: Incyte ID No: YCF22

<400> SEQUENCE: 7
agtgataatc cttacggaac aatgagcaca caatatattg atgagacagc atttgttcag      60
gctgagcaag gtaaaaccaa tctaatgttc tctgacgaaa agcaacaggc acgttttgag     120
ctcggtgttt ccatggttat ttataagtgg gatgcgttgg atgttgccgt agaaaacagt     180
tggggtggtc cagactcagc tgagaagaga gactggatta cagggattgt agtagacctt     240
ttcaaaaatg aaaagttgt tgacgccgct taatcgaag aaacgttact ttatgcaatg      300
atagatgaat ttgaaactaa tgttgaagac gactcggctt taccgattgc cgtggaggtc     360
atcaacatat ataacgactg tttcaattta aattataata aggtagaaaa attgtatttg     420
gaatggcaag aaaagcagag aactaaaaaa tcaaaagag ttgtgcatat tgagggtgat      480
gatgatgaag acgatgaaga tgtagaggac tatgatgacg aagatgaaga tgaagagatg     540
gacgaggttg tacctgactt agtatcgtct aaacctgaac caattgttga cgaagacggt     600
tttgaattgg ttcaaccaaa aggaagaaga agcactagt atcttcaaaa tctgtatatt      660
ataattgata gtgcgctgct tttttgcact tccagtaaga aatagcaaca aaattagata     720
aatctcggtg gagttatcca aaatatgtaa tatatcaa gaaagttacg tattaaacat       780
tggacttcta gaggagatct tcaatataga tttaaaggt gggcaatgca tcgctacgtg      840 aagatttta cttttcttca acatgtgtat tttttatgtt tcatatttt atattttgtg       900 tttgctaagg tctaatcgtt cagc                                            924

<210> SEQ ID NO 8
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F22S1

<400> SEQUENCE: 8
acggaacaat gagcacacaa tatattgatg agacagcatt tgttcaggct gagcaaggt       59

<210> SEQ ID NO 9
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F22S198

<400> SEQUENCE: 9
gactggatta cagggattgt agtagacctt ttcaaaaatg aaaagttgt tgacgccgc       59

<210> SEQ ID NO 10
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F22S425

<400> SEQUENCE: 10
gagaactaaa aaatcaaaaa gagttgtgca tattgagggt gatgatgatg aagacgatg       59
```

<210> SEQ ID NO 11
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F22S794

<400> SEQUENCE: 11
tagatttaaa aggtgggcaa tgcatcgcta cgtgaagatt tttactttc ttcaacatg    59

<210> SEQ ID NO 12
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F22S853

<400> SEQUENCE: 12 tgtattttt atgtttcata tttttatatt ttgtgtttgc taaggtctaa tcgttcagc    59

<210> SEQ ID NO 13
<211> LENGTH: 937
<212> TYPE: DNA
<213> ORGANISM: Candida albicans
<220> FEATURE:
<221> NAME/KEY: misc_feature
<223> OTHER INFORMATION: Incyte ID No: YCF23

<400> SEQUENCE: 13
atccgccaca taagatgcac aaaatgagcc tataacattg aattttatga tagaacgaaa     60
ggattgtgtt atttagaaca gagtatcagt atatcgtatg tcacagaaca acacaatcag    120
ctcaatgaat cctgaaagag cttacaacaa tgtaacgctg aaaaatttaa cagcatttca    180
gttattatct caaagagaaa acatatgcga gttattgaac ttggtagaaa gtacggaaag    240
acacaatagt attatcaatc ctgaaaggca aaggatgagt ttggaagaaa tgaaaaaaat    300
gctcgatgct ttgaaaaatg aaaggaaaaa gtaggaaaac gcaacattca caattgtaag    360
ctacaaaata ttgaatgtga atcctgcttc attacaaatg aagaatttca aagcgtatct    420
agttcaccaa aagtcacaat atcttattat tatttggaag cttttatatg catctaatgg    480
tcataaatcc catctcactt tataaaacaa gttaccgcga atgtatccag tgatacagaa    540
tagagtgtaa caaatgagaa taaaaatacc atattatcgt ttaattttgg tagggtacgc    600
taaaataaag tggtgtttgc gtctccatat aactaaaaag aattgaaatg gcctactatc    660
gattagacta ttcaggcatg gaagcagtaa gaacatttct tgattttgga aaaatgagat    720
tagattatta attattattg agtttgtgta tataatttat tttgcatatt tcataaagaa    780
attaaaatta gattattaaa tattaagttt cattagtgac attaaaagaa gaaaactgat    840
gttttgaaat gtgttaagca aagaatgatt aagacaatct caagctgctc taagcagtat    900
cttcgacagc ttgctctgct tcaggttcgg gttcgtg                             937

<210> SEQ ID NO 14
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F23S1

```
<400> SEQUENCE: 14
atccgccaca taagatgcac aaaatgagcc tataacattg aattttatga tagaacgaa        59

<210> SEQ ID NO 15
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F23S200

<400> SEQUENCE: 15
aacatatgcg agttattgaa cttggtagaa agtacggaaa gacacaatag tattatcaa        59

<210> SEQ ID NO 16
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F23S431

<400> SEQUENCE: 16
aagtcacaat atcttattat tatttggaag cttttatatg catctaatgg tcataaatc        59

<210> SEQ ID NO 17
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F23S805

<400> SEQUENCE: 17
aagtttcatt agtgacatta aaagaagaaa actgatgttt tgaaatgtgt taagcaaag        59

<210> SEQ ID NO 18
<211> LENGTH: 59
<212> TYPE: DNA
<213> ORGANISM: Candida albicans
<220> FEATURE:
<221> NAME/KEY: misc_feature
<223> OTHER INFORMATION: Incyte ID No: F23S846

<400> SEQUENCE: 18
aatgattaag acaatctcaa gctgctctaa gcagtatctt cgacagcttg ctctgcttc        59
```